(12) United States Patent  
Marple et al.

(10) Patent No.: US 6,520,673 B2
(45) Date of Patent: Feb. 18, 2003

(54) MIXING DEVICES FOR SAMPLE RECOVERY FROM A USP INDUCTION PORT OR A PRE-SEPARATOR

(75) Inventors: Virgil A. Marple, Maple Plain, MN (US); Daryl L. Roberts, Blaine, MN (US)

(73) Assignee: MSP Corporation, Minneapolis, MN (US)

( * ) Notice: Subject to any disclaimer, the term of this patent is extended or adjusted under 35 U.S.C. 154(b) by 0 days.

(21) Appl. No.: 09/733,108

(22) Filed: Dec. 8, 2000

(65) Prior Publication Data

US 2002/0071342 A1 Jun. 13, 2002

(51) Int. Cl.$^7$ .................................... B01F 9/00
(52) U.S. Cl. ....................... 366/213; 366/217
(58) Field of Search ................. 366/197, 209, 366/210, 211, 213, 214, 217, 219, 220

(56) References Cited

U.S. PATENT DOCUMENTS

| 1,077,456 A | * | 11/1913 | Forest |
| 1,148,786 A | * | 8/1915 | McKenney et al. |
| 1,755,763 A | * | 4/1930 | Barber |
| 1,913,979 A | * | 6/1933 | Farrington |
| 2,650,805 A | * | 9/1953 | Schaefer |
| 3,086,332 A | * | 4/1963 | Wentz |
| 3,614,434 A | * | 10/1971 | Horwitz et al. |
| 3,999,742 A | * | 12/1976 | Heyraud |
| 4,162,129 A | * | 7/1979 | Bartholemew, Jr. |
| 4,329,068 A | * | 5/1982 | Neuner et al. |
| 4,523,855 A | | 6/1985 | Walker |
| 4,789,245 A | * | 12/1988 | Morbeck |
| 4,907,893 A | | 3/1990 | Niemeck et al. |
| 5,197,802 A | * | 3/1993 | Miller et al. |
| 5,383,163 A | * | 1/1995 | Brunn |
| 5,496,110 A | * | 3/1996 | Geier et al. |

FOREIGN PATENT DOCUMENTS

FR  2 695 135 A1  8/1992

* cited by examiner

Primary Examiner—Charles E. Cooley
(74) Attorney, Agent, or Firm—Westman, Champlin & Kelly, P.A.

(57) ABSTRACT

A mixer supports a cradle holding an inlet component for a cascade impactor, and has sealing caps to close open ends of the component to trap a solvent in the component. The cradle is rotated by a motor for dissolving particles in the inlet component.

7 Claims, 3 Drawing Sheets

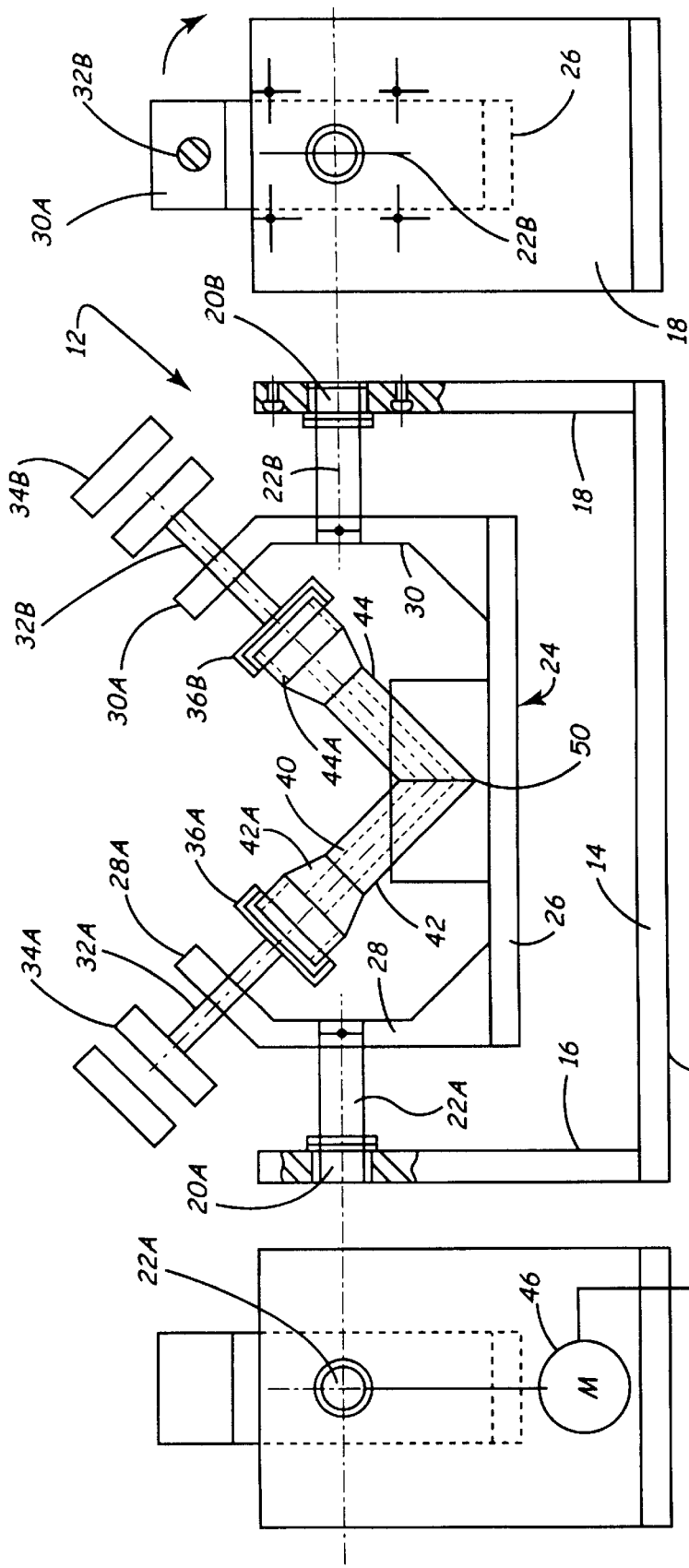

MIXING DEVICES FOR SAMPLE RECOVERY FROM A USP INDUCTION PORT OR A PRE-SEPARATOR

BACKGROUND OF THE INVENTION

Two sample recovery devices are disclosed which are used for agitating solvents in inlet components of impactors receiving particulate matter from inhalers to recover particles of interest clinging to walls of such components. The sample recovery devices are designed to assist laboratory personnel in the measurement of the size distribution of particulate matter emitted from metered-dose, dry-powder, and similar inhalers. Such inhalers are in common use for the treatment of asthma today and are increasingly important in the therapeutic delivery of pharmaceutical products of biotechnology.

Inhalers must be tested regularly both during laboratory development of new products and for quality control and assurance for commercially sold products. The testing includes the measurement of the size distribution of particles emitted by the inhalers. The United States Pharmacopeia (USP) and similar British, European, and Japanese regulatory documents describe the use of cascade impaction devices as the acceptable method for measuring size distribution. Further, these international compendia describe the inlet that must be used to introduce the particles into the cascade impactor. This inlet is known commonly as the USP Induction Port and is shown on page 1902 of USP 24, Section 601.

Because particulate matter accumulates in this induction port during each test of an inhaler device, the laboratory analyst doing the testing must quantify the mass of active drug material deposited in the induction port. Typically, this procedure involves washing the inside walls of the induction port with a solvent known to dissolve the active drug ingredient and in some manner insuring that all drug material is recovered from the inside walls of the induction port. The wash solvent is then analyzed, typically by high-performance liquid chromatography (HPLC), to quantify the drug material.

The procedure of removing the drug material from the walls of the induction port is typically an ad hoc one with no assurance that all material is recovered. Further, the complete washing of the walls can consume a minimum of 50 ml of solvent and up to 200 ml of solvent. Consequently, the active drug compound is diluted with solvent, and the analysis via HPLC is relatively insensitive to the presence of the drug material, compromising the accuracy of the overall test.

In addition, pre-separators are used in many impactors. Dry-powder inhalers typically contain large diluent particles along with the active drug material. These diluent particles would interfere with the functioning of the cascade impactor designed to recover the dry particles allowed to enter the impactor during a test. Consequently, when an analyst tests a DPI, a pre-separator is attached to the inlet of the cascade impactor. Some drug material accumulates in this pre-separator during testing, and the active drug material captured in the pre-separator must be quantified. This procedure requires washing with a known amount of solvent, typically 50 ml to 200 ml in prior art procedures, and/or shaking the device.

SUMMARY OF THE INVENTION

The present invention relates to sample recovery or mixing devices that allow a user to add a minimum amount of solvent to parts that have recesses and bends, and to mix the solvent, while unattended, with active drug material that has been clinging to the walls. This will thoroughly wash the walls, and cause the active drug material to be dissolved in the solvent. The handling of the solvent to recover the material of interest after this washing process is according to standards.

The sample recovery devices of the present invention include fixtures that will hold the induction port, on the one hand, and a pre-separator on the other, and will rotate these components with the solvent contained in the chambers or passageways, after capping or sealing the openings, so the solvent acts on the material clinging to the interior surfaces.

The mixing devices insure that all of the surface areas are contacted by the solvent during the mixing process, so that it is known that all of the active drug material has been dissolved and is available for analysis.

The mixing devices are made so that they will permit use of a minimum amount of the solvent, and will yet provide adequate mixing to insure that all of the active drug materials are released.

BRIEF DESCRIPTION OF THE DRAWINGS

FIG. 1 is a side elevational view of a mixing device utilized with a USP Induction Port;

FIG. 2 is a first end elevational view thereof;

FIG. 3 is a second end elevational view thereof;

DETAILED DESCRIPTION OF THE PREFERRED EMBODIMENTS

Figure 4:
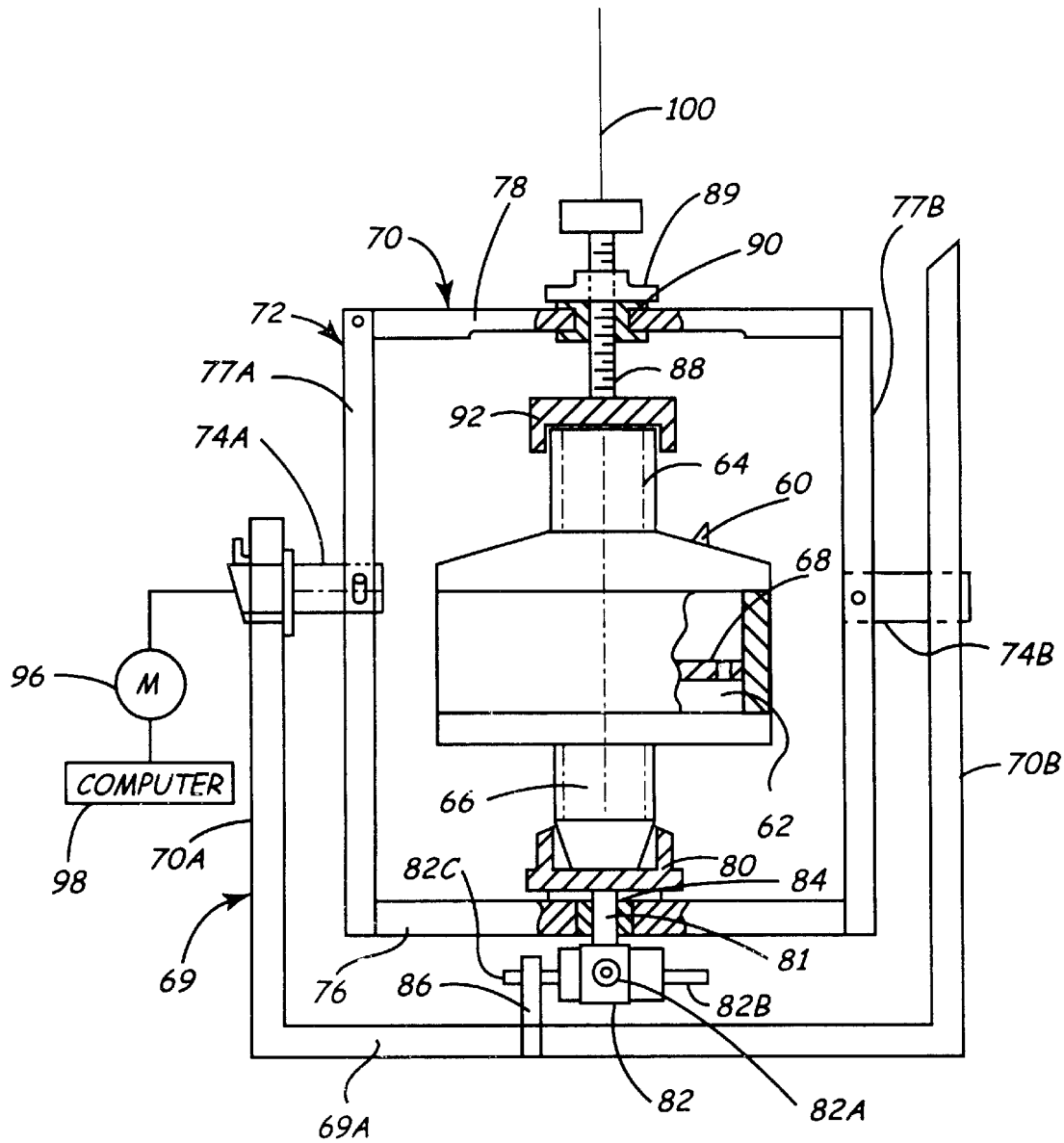
FIG. 4 is a side elevational view of a second mixing device adapted specifically for a pre-separator, for holding it in place for agitation.

Referring to FIG. 1, a stand or frame 10 is used as a frame for a sample recovery device indicated generally at 12. The stand has a base 14, and a pair of upright end members 16 and 18. The upright end members support bearings 20A and 20B, that in turn rotatably mount shaft portions 22A and 22B that are used for supporting a cradle 24. The cradle 24 has a base 26, and end supports 28 and 30 fixed to the base end supports, as shown, have bent wall portions 28A and 30A that are formed at a substantially 45° to the main portions of the end supports. These bent wall portions have threaded openings to support threaded rods 32A and 32B. The threaded rods have handles 34A and 34B for rotating them manually, and in addition, each of the rods 32A and 32B holds a cap or cup structure 36A and 36B which are on the inner sides of the bent wall portions 28A and 30A, and are positioned between the end supports 28 and 30.

A USP Induction Port is indicated at 40, and it has two tubular sections 42 and 44, at right angles to each other in a fixed assembly. The tubular sections 42 and 44 have standard open end connections or couplings shown at 42A and 44A. The tubular sections form a passageway through the interiors. In order to support the induction port 40 in the cradle 24, the screws 32A and 32B are backed out, so that the cup members 36A and 36B will permit the USP Inlet Port to slip into place, and then the screws are threaded down so that the cup members 36A and 36B cover the open ends of the couplings 42A and 44A. Prior to putting the inlet in position, and closing it off, a suitable amount of solvent is added to the interior chamber.

The cradle is then rotatably driven, by driving it with a motor 46 that can be operated through a computer control 48 as to the timing, speed, and the amount of rotation. Pneumatic motors could be used, but a stepper motor is shown as an exemplary embodiment.

The USP inlet will rotate around, and the solvent that is retained inside the tube will flow back and forth as the unit is rotated, and will contact all of the interior surfaces of the tubular sections 42 and 44.

In operation, the USP Inlet 40 is charged with a minimum amount of solvent, generally approximately 10 ml to 20 ml, and then the unit is put into place and the screws 32A and 32B are threaded so the caps 36A and 36B hold the inlet between the caps and seal the end openings.

The entire inlet and cradle assembly then is rotated, and the solvent will slosh or flow back and forth between both ends and the center portion 50 of the inlet, to insure adequate passage of the solvent over the surfaces to dissolve the particles of the active drug material.

Because the rotation is done by machine, the user not only saves time, because he can be at other tasks during the time that it is being used, but he avoids the tedium of having to shake the inlet port himself and to look into it to see if all the drug material has been recovered. Typically, the device can be rotated continuously or in one direction, or can be moved back and forth about the axis of the shafts 22A and 22B.

Figures 5, 6:
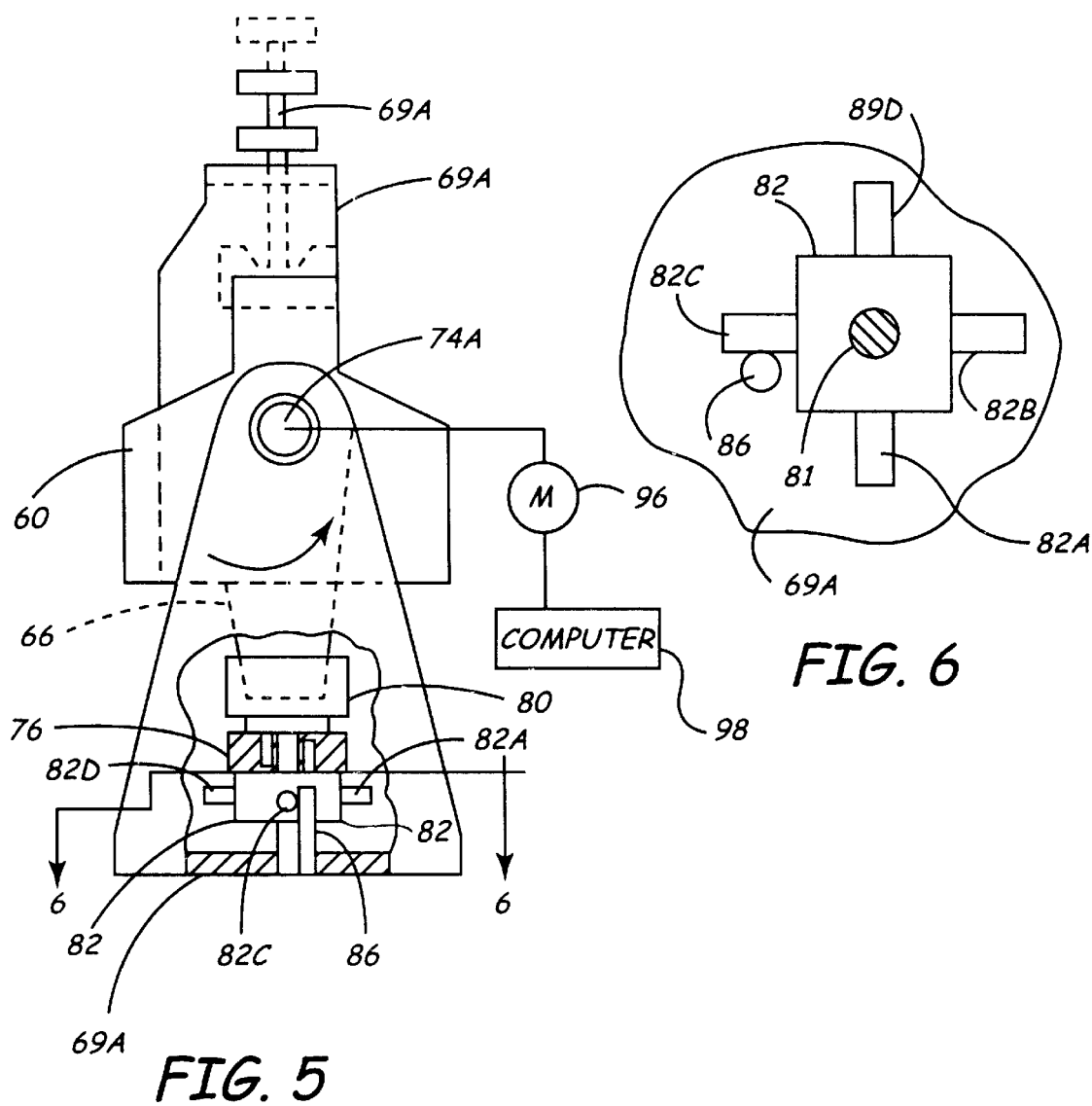
FIG. 5 is a side elevational view showing the mixing stand in position.
FIG. 6 is a schematic sectional view taken on line 6—6 in FIG. 5.

A second sample recovery device is shown in FIGS. 4 through 6, and in this instance, a pre-separator assembly 60 is being cleaned. It has an interior chamber, shown fragmentarily at 62, an inlet 64, and an outlet tube 66. In some of these pre-separators, there is an impaction plate in the center portions that is shown schematically at 68, but in any event the use is with the flow of an aerosol through the inlet 64, and the interior chamber 62 to the outlet 66.

The fixture of the present invention includes a frame 69 that has a base 69A supporting upright members 70A and 70B, that in turn rotatably mount a cradle 72. The cradle 72 has shafts 74A and 74B that are rotatably mounted on suitable bearings on the upright members 70A and 70B of the frame 69.

The cradle 72 has a lower support cross member 76, and an upper cross member 78 joining side members 77A and 77B. These cross members support hold cups for holding the pre-separator 60. The lower cross member 76 has an upwardly facing cup 80 that will receive the end of the outlet 66, as shown. This cup 80 is supported on the cross member 76 and has a shaft 81 that rotates in a bearing in the cross member 76. A turnstile drive member 82 is driven by the lower end of shaft 81 that has four arms that protrude at 90° to each other. Two of the arms 82A and 82B are shown in FIG. 4, and two of the arms 82C and 82D are shown in FIG. 5. The cup 80 is rotatably mounted in the bearing 84 so that the cup will freely rotate.

An upright post 86 is fixed to the lower frame member 68A and extends upwardly. This post 68 acts as a turnstile, as will be explained.

The upper cross member 78 rotatably supports a screw threaded shaft 88 that threads through a nut 89 that is mounted in a bearing 90 so the screw threaded shaft can rotate and also can be threadably adjusted. In other words, the bearing hub will permit the nut and shaft to rotate, but the screw threaded shaft 88 can be threaded, to move the cap shown at 92 vertically toward and away from the pre-separator housing 60.

In use, the device can be driven with a suitable motor 96 that is driven from a computer 98 in a normal manner. This too can be a stepper motor or could be a pneumatic rotary actuator as desired. It also could be a reversible DC motor.

The screw threaded shaft 88 has a manual handle 88A, can be threaded toward and away from the cross member 78.

When the pre-separator 60 is to be cleaned with a solvent, it is placed with the outlet 66 in the lower cup 80, and then solvent is put into the inlet 64, again using a limited amount of the solvent, probably in the range of 30–40 ml. Then the cup 92 is lowered into position to hold the pre-separator in a sealed position. Suitable gasketing materials can be used in the cups in this form of the invention, as well as the other form of the invention, to insure no leakage.

Once the pre-separator 60 is held between the cups 80 and 92, the motor 96 can be started and the unit can be rotated 360° about the shafts 74A and 74B. As it rotates, the post 84 will engage one of the arms 82A–82D and will rotate the pre-separator 60 about the upright axis, that is indicated at 100.

In this way, the pre-separator is indexed 90° about the upright axis for each revolution about the horizontal axis. If desired the pre-separator can be rotated a selected number of degrees and then rotated in a reverse direction for proper use of the solvent in dissolving the drug particles of interest.

The rotation about the vertical axis caused by the turnstile type post and cross member, insures that there are no dead zones inside the pre-separator that remain unwashed or untouched by the solvent. The user can also reverse the direction of the rotation about the horizontal axis to effect complete mixing.

The sample recovery device shown improve the repeatability and uniformity of the sample recovery process from the pre-separator and from the USP Induction Port.

Although the present invention has been described with reference to preferred embodiments, workers skilled in the art will recognize that changes may be made in form and detail without departing from the spirit and scope of the invention.

What is claimed is:

1. A sample recovery device for mounting and rotating an inlet component for a particle impactor about an axis, wherein particles may cling to an interior surface of the component, the inlet component having an interior chamber and first and second open ends open to the chamber, the device comprising a rotatable cradle supporting the inlet component, said cradle comprising a base member, a pair of side members supported on the base member and spaced apart sufficiently to receive the inlet component, the inlet component having two tubular members joined at substantially right angles to each other at a junction portion, the side members of the cradle having inwardly bent portions at an end thereof opposite from the base, and a pair of caps threadably mounted in the inwardly bent portions such that the axes of the threading of the caps is substantially coincidental with a respective axis of the two joined tubular members, said caps being movable toward and away from an inlet component on the cradle for sealing the respective open ends of the inlet component to permit retaining and supporting the inlet component on the cradle and being threadable for releasing the inlet component, and a drive to rotate the cradle a desired amount about an axis.

2. The sample recovery device of claim 1, wherein said caps have gaskets therein for sealing the open ends of the inlet component supported thereon.

3. A sample recovery device for moving an inlet component for a particle impactor about axis, the inlet component having an interior chamber defined by surfaces on which particles may cling, the inlet component comprising an L-shaped pair of tubes joined in a center portion and having first and second open ends open to the chamber and capable of receiving solvent for dissolving particles that cling to surfaces of the chamber, said sample recovery device comprising a support frame, a cradle rotatably mounted on said support frame about a cradle axis, said cradle comprising a base member, and a pair of upright end members fixed to the base member, a block on the base member for receiving the center portion of the tubes, a pair of caps mounted on the upright end members of the cradle and of size to receive the open ends of the inlet component, at least one of the caps being adjustable in spacing to form closures with the respective caps at both of the first and second open ends of the L-shaped pair of tubes to seal the interior chamber, and to urge the L-shaped pair of tubes toward the block for supporting the inlet component on the cradle, and a drive to rotate the cradle about the cradle axis relative to the support frame.

4. In combination, an inlet component for a sample recovery device, said inlet component having a central chamber and a pair of open ends, the inlet component having the interior surfaces on which particles may cling, and being capable of holding a solvent for engaging the particles when the inlet component is moved, and a cradle for supporting the inlet component, a pair of caps on the cradle for sealing both of the open ends of the chamber of the inlet component, a stand rotatably mounting the cradle for rotation about a cradle axis, and a drive for rotating the cradle a desired amount about the cradle axis while the inlet component is supported thereon and the open ends are sealed by the caps.

5. The combination of claim 4, wherein the component to be supported is a tubular member forming an L-shape, the caps having axes that are inclined relative to the axis of rotation of the cradle.

6. The combination of claim 4, wherein said cradle comprises a framework surrounding the inlet component, said framework having side members that are spaced apart and supported on the stand, and the framework having end members that are spaced apart and join the side members, the respective caps being mounted on the end members, the inlet component fitting between the end members and having inlet and outlet portions that fit into the respective caps.

7. The sample recovery device of claim 6, wherein said caps are rotatable about a common axis and a drive member for causing rotation of the caps and a supported inlet component about the common axis during portions of rotational movement of the cradle when driven by the drive.

* * * * *

UNITED STATES PATENT AND TRADEMARK OFFICE
CERTIFICATE OF CORRECTION

PATENT NO. : 6,520,673 B2
DATED : February 18, 2003
INVENTOR(S) : Virgil A. Marple and Daryl L. Roberts It is certified that error appears in the above-identified patent and that said Letters Patent is hereby corrected as shown below:

<u>Title page,</u>
Item [54], Title, should read:
-- DEVICES FOR SAMPLE RECOVERY FROM INLET COMPONENTS OF IMPACTORS --.

Signed and Sealed this

Sixth Day of April, 2004

JON W. DUDAS
*Acting Director of the United States Patent and Trademark Office*